(12) United States Patent
Offermann et al.

(10) Patent No.: US 7,763,272 B2
(45) Date of Patent: Jul. 27, 2010

(54) SUPPORT MATERIAL FOR TISSUE ENGINEERING, FOR PRODUCING IMPLANTS OR IMPLANT MATERIALS, AND AN IMPLANT PRODUCED WITH THE SUPPORT MATERIAL

(75) Inventors: Peter Offermann, Liegau-Augustusbad (DE); Hartmut Worch, Dresden (DE); Wolfgang Pompe, Hartha (DE); Michael Gelinsky, Dresden (DE); Gerhilt Schmack, Dresden (DE); Gerald Hoffmann, Wilsdruff (DE); Uwe Köckritz, Dresden (DE)

(73) Assignee: Technische Universität Dresden, Dresden (DE)

( * ) Notice: Subject to any disclaimer, the term of this patent is extended or adjusted under 35 U.S.C. 154(b) by 1614 days.

(21) Appl. No.: 10/799,329

(22) Filed: Mar. 12, 2004

(65) Prior Publication Data
US 2004/0266000 A1    Dec. 30, 2004

(30) Foreign Application Priority Data
Mar. 13, 2003  (DE) .................. 103 12 144

(51) Int. Cl.
*A61F 2/02* (2006.01)
(52) U.S. Cl. ............................................. 424/426
(58) Field of Classification Search .................. None
See application file for complete search history.

(56) References Cited

U.S. PATENT DOCUMENTS

| 4,016,303 | A | 4/1977 | Poirier et al. |
| 5,658,343 | A | 8/1997 | Häuselmann et al. |
| 6,224,893 | B1 * | 5/2001 | Langer et al. ............... 424/423 |
| 6,280,814 | B1 | 8/2001 | Offermann et al. |
| 2001/0010022 | A1 | 7/2001 | Dauner et al. ............ 623/23.71 |

FOREIGN PATENT DOCUMENTS

| DE | 2533682 | 2/1977 |
| DE | 19635214 | 3/1998 |
| EP | 0692227 | 1/1996 |
| EP | 0 984 745 | 3/2000 |
| WO | 87/00394 | 1/1987 |

* cited by examiner

*Primary Examiner*—Carlos A Azpuru
(74) *Attorney, Agent, or Firm*—Gudrun E. Huckett

(57) ABSTRACT

A scaffold for tissue culture and cell culture and for producing implant materials, in particular bone, cartilage or skin replacements or extra-corporal organ replacements or for other applications in medicine or biotechnology is made of biocompatible materials. It has at least one base material which is electrostatically flocked with fibers on at least one side. Through the electrostatic flocking the fibers are arranged almost perpendicularly on the surface of the base material and exhibits a high fiber pull-out resistance. The scaffold provides an elastic growth lattice, which is stable against compression, for cell colonization in vitro or the ingrowth of cells in vivo. Implants or implant materials can be produced with the scaffold.

27 Claims, 5 Drawing Sheets

SUPPORT MATERIAL FOR TISSUE ENGINEERING, FOR PRODUCING IMPLANTS OR IMPLANT MATERIALS, AND AN IMPLANT PRODUCED WITH THE SUPPORT MATERIAL

BACKGROUND OF THE INVENTION

The invention relates to a support material for tissue culture and cell culture (tissue engineering) for the production of implant materials, in particular bone, cartilage or skin replacements or extra-corporal organ replacements or for other applications in medicine or biotechnology. The invention further relates to an implant produced with the scaffold.

It is already known to cultivate cells on support material (scaffold) and use the thereby produced tissue culture as a tissue replacement. For example, gels, fiber materials, porous ceramics or other two- or three-dimensional structures are used as scaffolds. The treatment of different tissues, for example, cartilage, that are defective through injury, wear or sickness by means of grown tissue cultures is already known. For this purpose, endogenous cells are introduced, for example, into three-dimensional scaffolds, proliferated in vitro, and the material so produced is implanted in the body. The support materials used in biocompatible implants have substantial influence on the colonization, cell growth and future function of the implant.

Fiber materials offer large surfaces for contact with cells and form open-pored structures, which are necessary for the supply of the cells with nutrient solution. Today, non-woven materials are often used, which however show disadvantageous inhomogenities in their structure. Thus, cells will grow only very slowly through larger free spaces between the fibers. In areas where the fibers lie very tightly together, the cell density is in contrast very low. The organisation of the fiber arrangement in non-woven structures is only possible to a limited extent due to the high variance of the fiber orientation. Even though textile materials made out of threads are very well structured (see above), the distances between the fibers are extremely variable. Within the threads, which usually consist of 20 to 200 fibers each, the fibers lie extremely close together, and very large distances often exist between the threads.

Scaffolds made from textile materials, particularly from non-woven materials, fiber textiles or knitted textiles, show a very low compressive stability due to the predominantly horizontal arrangement of the fibers. For example, a melt-blown process for the production of three-dimensional air-intermingled non-woven substances is known from DE 199 59 088. The non-woven substances have pore sizes between 20 μm and 500 μm and a porosity of <95%.

DE 197 21 661 A1 discloses rods arranged in a three-dimensional lattice for the production of bone and cartilage replacement structures for immediate use in vivo. These rods consist of biopolymeric, thermoplastic materials and are built up layer by layer to a three-dimensional lattice by means of selective laser sintering from a layer in powder form or a three-dimensional printing (3-DP) process, which is similar to the functional principle of an ink-jet printer.

SUMMARY OF THE INVENTION

An object of the present invention is to provide a further support material for tissue culture and cell culture and for the production of implant materials and implants, respectively, and an implant produced from the support material.

According to the invention, the object is solved by a scaffold for tissue and cell culture and for the production of implant materials or implants, wherein the scaffold contains a base material, which is electrostatically flocked with fibers on at least one side.

The scaffold according to the invention consists entirely of biocompatible materials, that is, materials which are innocuous and compatible with biological tissue. The materials are selected preferably in such a way that they resemble as much as possible the body's own materials and structures without being immunogenic or allergenic. At the same time, the materials are chosen in such a way that they satisfy the demands of the flocking process.

Through the electrostatic flocking the fibers are arranged almost perpendicularly on the surface of the base material. Advantageously, the high fiber pull-out resistance achieved through electrostatic flocking prevents the detachment of the fibers from the base material. Advantageously, the scaffold according to the invention provides an elastic growth lattice, which is stable against compression, for cell colonization in vitro or the ingrowth of cells in vivo. Together with the base material, the fibers take on the function of the extra-cellular matrix which occurs in natural tissue. For this purpose, the fiber density of over 100 fibers/mm$^2$, preferably 150 to 500 fibers/mm$^2$, is very high compared to flocked structures which are known from other technological areas.

The mean distances between the biocompatible short fibers in the scaffold according to the invention (measured between the axes of the fibers) lie between 40 μm and 250 μm, depending on the cell types for which the scaffold is to be used. Preferably, the fibers on the base material have a mean distance from 40 μm to 130 μm. The interspaces thus formed between the fibers are optimal for the colonization of the scaffold with cells.

The high compressive strength ($\sigma_D$ over 0.1 MPa, linear elastic behavior), and the high compressive module (E over 0.2 MPa) of the scaffold are achieved through the almost perpendicular alignment of the fibers and the high flocking density. The attainable flocking density is the higher the shorter the fibers used for flocking are. With fibers that are 1 mm long it is preferably 150 to 250 fibers/mm$^2$, with fibers that are 0.5 mm long it is preferably 300 to 400 fibers/mm$^2$.

The denser the flocking and the shorter the fibers, the less the fibers can buckle laterally under pressure, since they are prevented from doing so by the neighboring fibers.

The biocompatible scaffold material according to the invention is produced according to the process of electrostatic flocking known from textile engineering. In this connection, biocompatible fibers are attached to a biocompatible surface material almost perpendicularly. The electrostatic flocking is carried out preferably with direct current. To achieve the high fiber density according to the invention, the electrostatic field strength must be varied. Preferably, the base material on the side to be flocked will be coated with adhesive for the electrostatic flocking. The coating with adhesive is dispensable, when the base material itself has a sticky surface.

In a preferred embodiment of the invention, the base material is flocked in a freely defined pattern. Through defined areas with and without flocked fibers, the colonization with cells is regulated. The cells preferably colonize the flocked areas, between and on the fibers. The base material is flocked on one or more sides. A partial flocking or a flocking in freely defined patterns is achieved by partially applying an adhesive, e.g. by means of templates, before flocking.

In a preferred embodiment of the invention, the base material, adhesive and/or fibers consist of a resorbable material. Resorbable material is to be understood, in this context and in the following, as a material that, after implantation in the body, is slowly degraded by biological and biochemical processes or slowly dissolves. A partial resorption of the materials can also occur during the cell cultivation in vitro.

As a resorbable material for the base material, preferably a membrane or tape made from collagen or collagen derivatives is chosen, including mineralized collagen or other components of the extra-cellular matrix. In a further embodiment of the invention, the base material is a membrane or a fiber material, non-woven material or woven material consisting of resorbable biopolymers (such as, for example, chitosan, hyaluronic acid, mineralized and/or non-mineralized collagen or collagen-hyaluronic acid composites), resorbable aliphatic polyesters (e.g. polylactide, polyglycolide, polyhydroxybutyrate, polycaprolactone) or their copolymers and derivatives.

In an alternative embodiment of the invention, the base material is comprised of a non-resorbable biocompatible material, such as, for example, a biocompatible metal (titanium, a titanium alloy, steel etc.), plastic (polymethylmethacrylate, polystyrene, polycarbonate etc.), ceramics (calcium phosphate, aluminum oxide etc.), glass or carbon (carbon fiber composites etc.).

Preferably, the base material has a flat, wavy or curved form, particularly in the form of a membrane (tape). In an alternative embodiment, the base material is a three-dimensional molded body or hollow body. Preferably, the base material has a profiled surface. The base material is preferably structured such that it takes up forces and supports the scaffold under load.

In one embodiment of the invention, the base material is pierced by punching or by means of a water jet or laser. Preferably, the holes are introduced into the base material after flocking. Piercing after flocking has the advantage that the flocking fibers at the edge of the holes are arranged almost perpendicularly.

As resorbable adhesive preferably gelatine, a collagen gel, alginate gel, hyaluronic acid solutions, or chitosan solutions are used. However, other biocompatible materials are conceivable also as adhesives when they exhibit a certain electrical conductivity and meet the demands of the electrostatic flocking process and thereby are suitable for the production of a suitable adhesive bond between base material and flocking fiber. Preferably, the adhesive is crosslinked after flocking. Crosslinking is achieved by means of chemical crosslinking agents, such as, for example, EDC (N'-(3-dimethylaminopropyl)-N-ethylcarbodiimide hydrochloride) or by other known methods, for example by means of UV- or gamma irradiation. Crosslinking is performed in particular when using gelatine, a collagen gel or hyaluronic acid as an adhesive, in order to avoid a quick dissolution of these adhesives in an aqueous environment as well as a softening during cell culture at 37° C. or after implantation. At the same time, the bonding between fibers, adhesive and base material is strengthened through the crosslinking agent. Preferably, the base material and the fibers have hydrophilic surfaces in order to achieve a good wetting with the adhesive.

Preferably, the fiber materials are comprised of resorbable aliphatic polyesters, for example, polylactide (PLA), polycaprolactone, polyhydroxybutyrate and polyglycolide, or their derivatives and copolymers. In this connection, the term polyhydroxybutyrate (PHB) includes β- and γ-PHB as well as their copolymers. Non-resorbable fiber materials, for example polyacrylate, polyamide, polypropylene, polytetrafluorethylene, cellulose, viscose or other cellulose derivatives, non-resorbable or slowly resorbable polyesters or combinations of these materials, are used in another preferred embodiment as materials for the fibers. Aside from organic polymers, inorganic materials such as glass, ceramics, $SiO_2$, carbon or metals or mixtures are employed.

The fiber materials must exhibit the known characteristics for the electrostatic flocking, for example a sufficient electrical surface resistance of $10^6$-$10^8$ Ω, that is achieved, if necessary, through suitable preparations when producing the threads or subsequently. The electrical resistance of the flocking fibers influences above all their charge and flight behaviour as well as the evenness of the flocked surfaces. Additionally, the geometric relationship between fiber diameter and fiber length has a substantial influence on the processing characteristics in the flocking process. Flocking fibers with a fiber length between 0.3 mm and 8 mm can be processed. Preferably, the individual fibers have a length between 0.3 mm and 3 mm, particularly between 0.5 and 1.5 mm. The diameter of the individual fibers lies preferentially between 10 μm and 200 μm. The shorter the fibers employed, the higher the compressive stability of the scaffold.

In preferred embodiments of the invention, fibers made of different materials with different diameters and/or lengths are combined. In this connection, long flocking fibers are supported by short fibers. Through the combination of fibers of differing lengths, the attainable fiber density is increased and an uneven, structured surface achieved.

In a further preferred embodiment of the invention, hollow fibers having open pores or closed pores are employed to reduce the fiber mass and raise the compressive elasticity.

In another embodiment of the invention, the biocompatible scaffold is at least partially mineralized. Such a mineralized scaffold is particularly suitable for use as a bone replacement material. In the case of a partial mineralization, only individual components are mineralized preferentially, particularly the base material. The scaffold or components thereof are mineralized preferentially with hydroxyapatite (the calcium phosphate phase of bone). The production of a partially mineralized scaffold is achieved preferably by using mineralized materials, e.g. a mineralized collagen tape, as base material when constructing the scaffold.

In a further embodiment of the invention, the ready-formed biocompatible scaffold is mineralized. For this mineralization a known process for the mineralization of collagen or rather a collagen tape is applied, analogous to, for instance, the deposition of hydroxyapatite from simulated body fluid (SBF), (S.-H. Rhee, J. Tanaka: Hydroxyapatite coating on a collagen membrane by a biomimetic method. J. Am. Ceram. Soc. 1998, 81, 3029-3031).

In one particular embodiment of the invention, active substances are bonded to the base material, adhesive or fibers. Active substances are to be understood in this connection to include, for example, pharmaceutical substances, peptides, proteins, antibodies, growth factors, cytokines, chemokines, oligonucleotides, nucleic acids such as cDNA, or nucleic acid derivatives. The bonding of these substances to the respective material is achieved preferably by covalent bonding to the base material or mixing with the base material or adhesive before flocking. Alternatively, these substances are bonded to the scaffold after flocking. Besides covalent bonding, the active substances can be bonded to the scaffold or its components, e.g. the fibers, adhesively or by using other methods.

A further subject matter of the invention is a multilayered support material (multilayer scaffold) in which at least two of the biocompatible scaffolds described above are connected with one another.

As a result of the multilayered layer structure, defined cell-specific pore distances and distances between layers are generated by means of the electrostatic flocking. The flocking fibers act thus as spacers in the multilayered structure.

In a preferred embodiment of the multilayered support structure, the individual scaffolds are stacked on top of one another. In this connection, the distance between the base materials of the scaffolds arranged in layers is a result of the fiber length between the base materials. Preferably, the connection between the scaffolds consists of an additional adhesive layer. The materials named above are used as the adhesive.

In a further embodiment of the multilayered structure, the individual scaffolds are inserted into one another with their fiber layers. By inserting them into one another, the fiber layers form a common fiber layer in which the fiber densities are add. The insertion of the fiber layers into one another advantageously holds both scaffolds together without an additional adhesive layer.

In a particularly preferred embodiment, the multi-layered biocompatible scaffold contains hollow spaces, which are connected with one another or isolated from one another. Preferably, these hollow spaces form a cavity system formed from cavities that are straight, canal-shaped and/or meander-shaped and connected to one another.

These cavities are formed, e.g. when combining layers to form a multilayered structure, by defined areas free of flocking fibers on the base material and preferably through the use of defined perforated base materials. These continuous and preferably three-dimensional interconnected cavities serve, among other things, for supplying nutrients and oxygen to the cells and enable a rapid ingrowth of blood capillaries after implantation.

Advantageously, the biocompatible material according to the invention can be used as an implant material, for the production of cell implants and tissue implants, as well as in cell culture or tissue culture and also for the production of an extra-corporal organ-replacement.

When used as an implant material, in a preferred embodiment, the scaffold is implanted into the body without prior colonization with cells. After implantation, the scaffold, in this case in vivo, will be colonized by cells that originate from the surrounding natural tissue. In this connection, these cells grow into the interstitial spaces between the flocking fibers. If the scaffold is constructed completely from resorbable materials, it is resorbed advantageously within a few weeks to a few years, preferably within a few months, after implantation and replaced by endogenous tissue.

In a further preferred embodiment of the invention, the scaffold is colonized with cells in vitro. For this purpose, cells are cultivated on the scaffold for a few days to weeks. During this time, cells colonize the scaffold, that is, they grow into the scaffold. This scaffold colonized by cells is either implanted in the body as a tissue replacement in a tissue engineering sense, or it remains outside the body for other tasks such as extra-corporal organ replacement (e.g. a temporary liver replacement).

In a further embodiment of the invention, the base material and/or adhesive of the scaffold is removed after or during the colonization with cells, when the cells have stabilized the scaffold sufficiently through the production of newly-formed extra-cellular matrix. The removal of the base material or adhesive is carried out mechanically, chemically and/or enzymatically. If the base material and/or the adhesive consist of collagen, the removal is aided preferably by adding collagenases.

A further part of the invention is an implant, which contains the biocompatible scaffold. This implant consists of a single-layered or multilayered scaffold and preferably an envelope structure, which surrounds the scaffold. The envelope structure is constructed from biocompatible materials. Preferably, it is comprised of textile fibers in the form of a woven fabric, knitted fabric, crocheted fabric, embroidered fabric or fleece. The fibers for the envelope structure consist preferentially of biopolymers such as chitosan, polylactide, polycaprolacton, polyhydroxybutyrate and polyglycolide, or their derivatives and copolymers. Alternatively, the envelope structure consists of a perforated film (or a perforated film tube), which is comprised preferably of the biopolymers named above. In a further embodiment, the envelope structure consists of a biopolymer tape made out of collagen-hyaluronic acid composites or hydroxyapatite-collagen composites.

The implant is preferably colonized with cells before implantation. For this purpose the implant is colonized with cells, as described above for the scaffold. The envelope structure offers an additional support function and facilitates the handling of the implant during cell culturing and during surgery.

Another component of the invention is a process for the manufacture of a cell culture or tissue culture or an implant material with the following steps:
  a) Production of a scaffold through the electrostatic flocking of a base material with fibers on at least one side,
  b) Incubation of the scaffold with cells for the colonization of the scaffold with cells and formation of an extra-cellular matrix, wherein the base material (1) is removed after the formation of the extra-cellular matrix where appropriate.

For the flocking step, in the case that the base material itself does not have a sticky surface, the base material is first coated with adhesive.

The fibers and cells are held together by the extra-cellular matrix that is generated by the cells. The base material—initially required as a scaffold for the fibers during flocking—and, if necessary, the adhesive are therefore preferably removed after the formation of the extra-cellular matrix.

The composition of the extra-cellular matrix depends of the cell type used for cell colonization. It resembles the extra-cellular matrix which occurs in natural tissues. Known components of the natural extra-cellular matrix are, for example, structural proteins such as collagens or elastin, adhesion proteins such as laminin or fibronectin, as well as polysaccharide components such as hyaluronic acid or glycoproteins.

The removal of the base material or adhesive is carried out mechanically, chemically and/or enzymatically. If the base material and/or the adhesive consist of collagen, the removal is aided preferably by adding collagenases.

A further subject matter of the invention is an implant material which contains cells and an extra-cellular matrix. This implant material is produced by the steps:
  a) Production of a scaffold through the electrostatic flocking of a base material (1) with fibers (3) on at least one side,
  b) Incubation of the scaffold with cells for the colonization of the scaffold with cell and formation of an extra-cellular matrix,
  c) Removal of the base material (1) after the formation of the extra-cellular matrix Through electrostatic flocking the fibers are advantageously arranged almost perpendicularly and parallel to each other in this implant material. During the incubation, cells settle predominantly on and between the fibers and build an extra-cellular matrix. In this connection, the cell colonization and the construction of the extra-cellular matrix are directed by the flocking fibers. Advantageously, the result is an oriented tissue structure, in which cells and the extra-cellular matrix are aligned relative to one another similarly as in a natural tissue.

The implant material thus produced is suitable as a tissue replacement, particularly as a replacement for cartilage or skin. The cells used for cell seeding are selected in this connection in accordance with the tissue to be replaced. Thus, the scaffold is colonized for example with keratocytes and/or fibroblasts to produce a material for skin replacement. To produce a material for cartilage replacement, chondrocytes are chosen for cell colonization.

The high compressive elasticity of the scaffold advantageously allows the simulation of a mechanical loading of the cell formation in vitro. For this purpose, pressure is applied on the surface of the scaffold during the incubation of the scaffold in accordance with a preferred embodiment of the invention. In an alternative embodiment, the application of pressure is complemented or replaced by an application of ultrasound.

In this connection, the mechanical loading in vitro can be chosen advantageously such that it approaches the natural loading of cells in vivo, such as, for example, that of chondrocytes in joint cartilage. In this connection, the flocking fibers simulate the natural extra-cellular matrix of the tissue and take up a part of the load.

BRIEF DESCRIPTION OF THE DRAWINGS

The invention is illustrated in more detail with the aid of the following drawings and examples. It is shown in.

Figure 1:
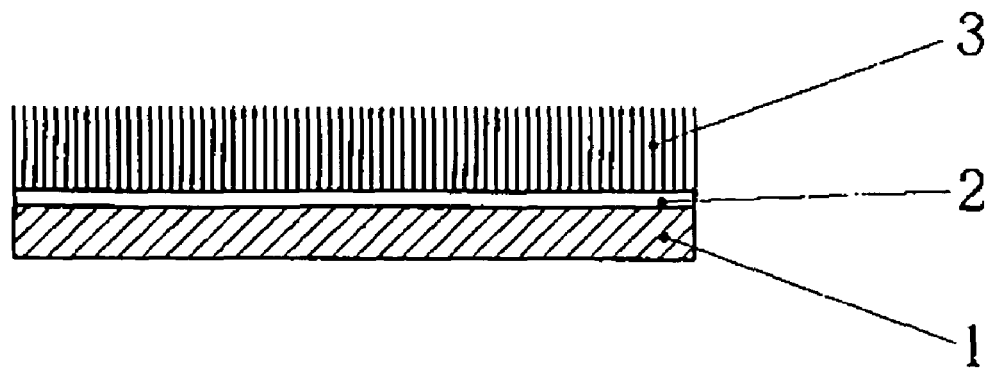
FIG. 1. a sectional view of a scaffold.

In the attached drawings the following reference numerals are used:

1 base material
2 adhesive
3 fibers
4 areas without fibers on the base material or in the scaffold
5 cavities

DESCRIPTION OF PREFERRED EMBODIMENTS

The scaffold represented in FIG. 1 consists of a flat base material 1, which is coated with an adhesive layer 2 on one side and electrostatically flocked with fibers 3 that are 1 mm long.

A mineralized hydroxyapatite-collagen-tape with a diameter of 7 cm and a mean thickness of 0.2 mm was selected as a biocompatible, resorbable base material 1. The hydroxyapatite-collagen-tape is produced from mineralized collagen (EP 0 945 146, EP 0 945 147, U.S. Pat. No. 6,384,196, U.S. Pat. No. 6,384,197, J.-H. Bradt, M. Mertig, A. Teresiak, W. Pompe: Biomimetic mineralization of collagen by combined fibril assembly and calcium phosphate formation. Chem. Mater. 1999, 11, 2694-2701), as described in R. Burth, M. Gelinsky, W. Pompe: Collagen-hydroxyapatite tapes—a new implant material, Tech. Textile 1999, 8, 20-21.

The adhesive 2 consists of Pharma-Gelatine, DGF Stoess AG, Eberbach, Germany, a biocompatible, resorbable material.

The fibers 3 have a length of 1 mm and a diameter of 0.03 μm. The fiber material is comprised of polyhydroxybutyrate, a biocompatible, resorbable material with a Young's modulus up to 7 GPa. After a surface modification by means of alkaline hydrolysis (L. Rouxhet a.o. "Adsorption of albumin, collagen, and fibronectin on the surface of PHB/HV and of PCL films modified by an alkaline hydrolysis and of PET track-etched membranes", J. Biomater Sci. Polymer Edn. 9. (1998) 12, 1279-1304), these short fibers sufficiently satisfy the demands of flocking technology for an electric surface resistance of $10^6$-$10^8$ Ω.

The procedure for the manufacture of the scaffold is as follows:

The Pharma-Gelatine 2 is mixed with distilled water in the ratio 5 g: 100 ml, heated to 60° C. with stirring by means of a magnetic stirrer MR 3001 K and temperature regulator EKT 3001, Heidolph Instruments GmbH & Co. KG, Schwabach, Germany, and cooled to 25° C. after complete dissolution of the gelatine.

Threads are generated in a melt-spinning process according to the textile-physical specifications in an online spin-stretching process, appropriately treated, and subsequently cut to fibers 3 that are 1 mm long.

A laboratory flocking device from Maag Flockmaschinen GmbH, Iserlohn, Germany, is used for the electrostatic flocking. The system was adapted for the processing of short fibers 3 that are 1 mm long through the selection of a suitable sieve electrode with a hole diameter of 1.2 mm and the adjustment of the flocking distance to 125 mm.

The Pharma-Gelatine 2 is evenly applied to the base material 1 by means of a silk-screen template with an adhesive thickness 2 of 0.4 mm. Subsequently, the base material 1 coated with Pharma-Gelatine 2 is loaded into the flocking device. The flocking voltage is raised continuously from 20 kV to 60 kV within 20 seconds to achieve high flocking densities. The high-voltage field is maintained for a further 10 seconds in order to detach excess short fibers 3 from the scaffold through the field effect.

Subsequently, the hydroxyapatite-collagen tapes thus flocked with biocompatible and resorbable short fibers 3 are freeze-dried. So that residual stresses which occur during the drying process do not lead to warping of the tape, they are weighed down with porous pressure plates during drying. The thickness of the adhesive shrinks to 0.02 mm as a result of freeze-drying.

After freeze-drying, the adhesive layer 2 of the now flocked hydroxyapatite-collagen tape is chemically crosslinked by placing it in a 1% solution of ECD N'-(3-dimethylaminopropyl)-N-ethylcarbodiimide hydrochloride from Sigma-Aldrich Chemie GmbH, Munich, Germany, in 80% Ethanol for 4 hours. During the crosslinking, covalent bonds are formed between the collagen molecules of the gelatine adhesive layer 2 and, to a lesser extent, also between the collagen molecules of the adhesive layer and the base material 1, which additionally stabilize the scaffold.

The scaffold material thus produced is characterized by a flocking fiber density of 290 fibers/mm$^2$, a compressive strength of $\sigma_D$=0.13 MPa (linear elastic behaviour), a compressive modulus of E=0.25 MPa, a fiber pull-out strength of $\sigma_F$=0.41 Mpa, and a fiber spacing of between 35 μm and 70 μm.

Advantageously, the high fiber pull-out strength prevents a detachment of individual fibers 3 from the base material 1 under tensile loading.

Particularly advantageous is the high compressive stability and the elasticity of the scaffold material. These values satisfy the mechanical demands which are placed on supporting structures in natural tissues and organs, including cartilage.

For the cell seeding, a sample with a diameter of 13 mm is punched out of the thus produced flocked hydroxyapatite-collagen tape 1. The sample is sterilized by irradiation with gamma radiation and afterwards placed in 5 ml sterile cell culture medium (DMEM, Sigma GmbH, Munich, Germany) for 24 hours. The medium is changed every 6 hours.

Subsequently, the sample is taken out of the medium and dried to some extent by placing it on a sterile, absorbent towel. The sample is now transferred to a customary 24-well cell culture plate with the flocked side up and a suspension of $1\times10^5$ primary human chondrocytes in 1 ml cell culture medium is applied with a pipette. The cell culture plate is now incubated for 24 hours in a typical cell culture incubator under standard conditions. During this time the chondrocytes become adhered to the scaffold. Subsequently the thus seeded scaffold is transferred to fresh medium and cultivated, including changing of the medium three times weekly, under standard conditions until further use.

Figure 2:
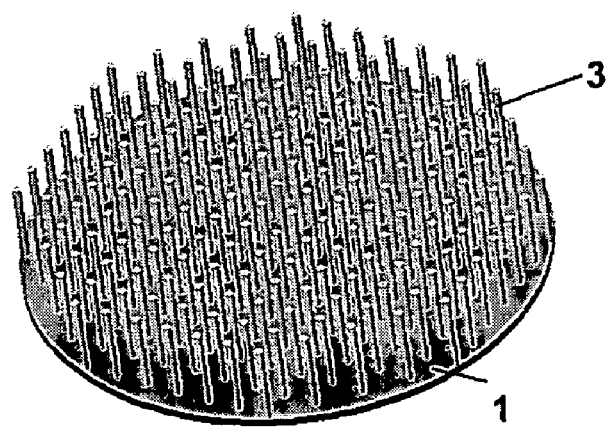
FIG. 2. a three-dimensional illustration of a scaffold.

The scaffold in FIG. 2 is identical to that in FIG. 1. The adhesive layer 2 is not shown for reasons of clarity.

Figure 3:
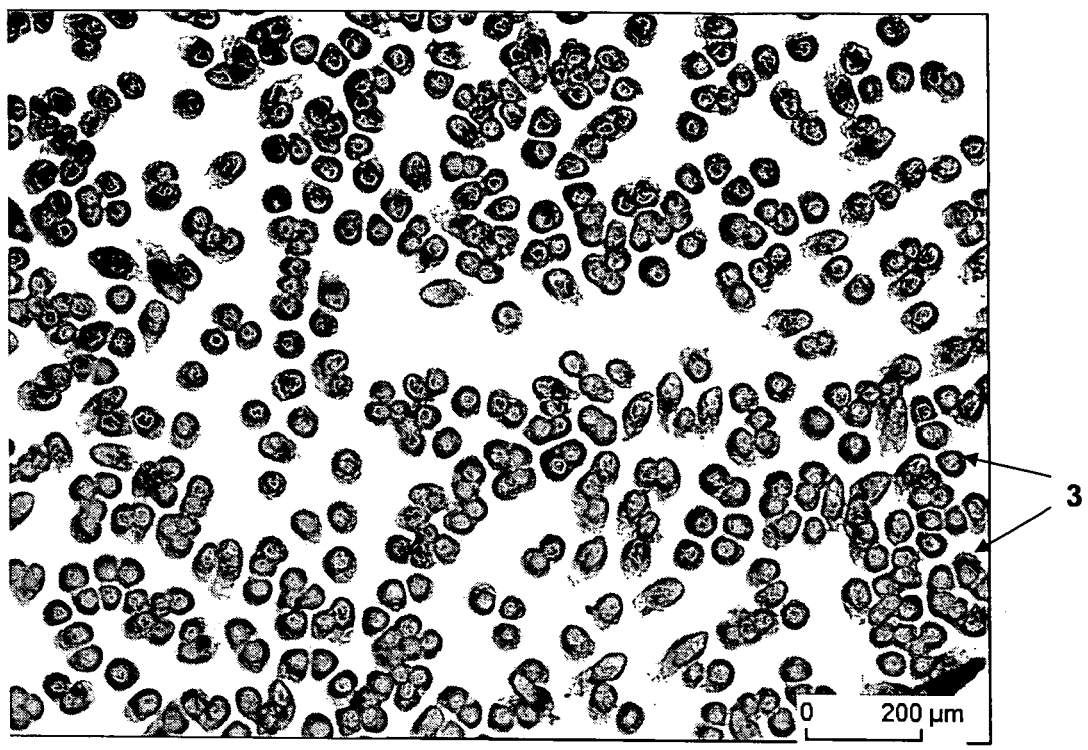
FIG. 3. a light-microscope micrograph of a horizontal cross-section through a scaffold.

For the light microscope micrograph (FIG. 3.), the scaffold was embedded in epoxy resin (SpeciFix-20, Struers) parallel to the surface and prepared for optical evaluation of the fiber distances with a grinding-polishing procedure. The light microscope micrograph was carried out using the reflected- and transmitted-light microscope AxioTech 100, Zeiss (50×). From this micrograph, the arrangement of the fibers 3 on the surface of the base material 3 is apparent. FIG. 3 shows that the distribution of the fibers provides a regular distribution of the interspaces between the fibers 3, which interspaces, with a diameter from 40 μm to 130 μm, have the optimal size for the colonization with cells.

Figure 4:
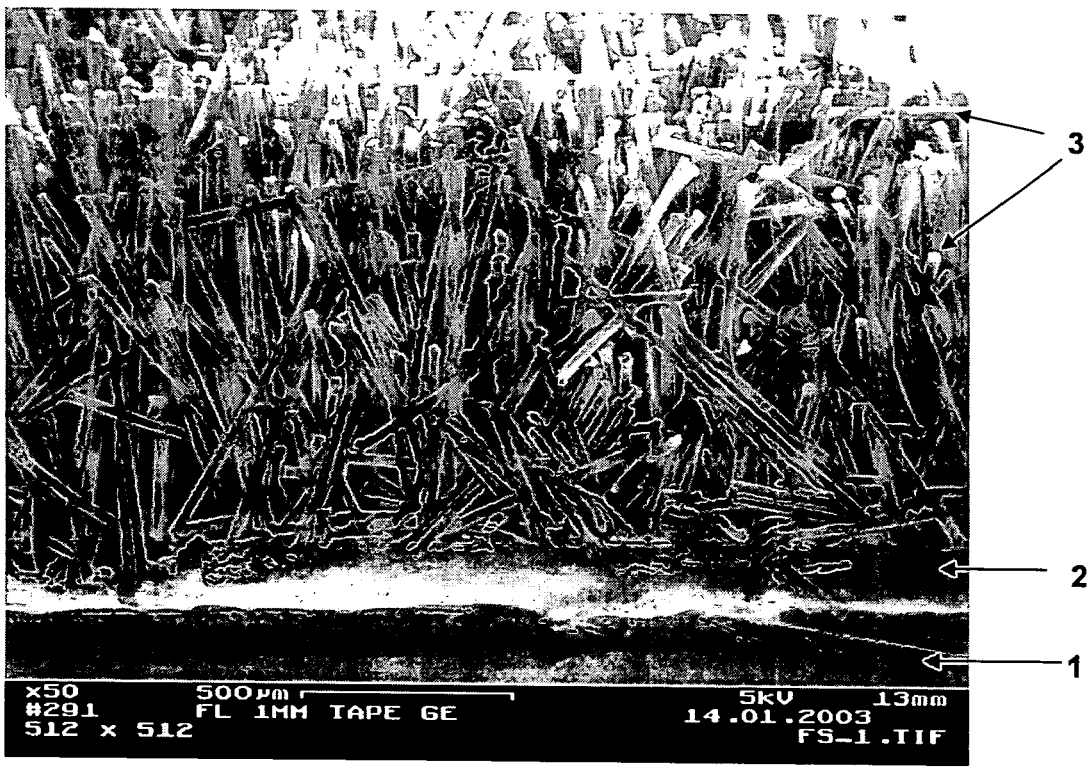
FIG. 4. a raster electron microscope micrograph of a scaffold from the side.

For the raster electron micrograph (FIG. 4), a sample was cut out of a scaffold with scissors; this scaffold had been produced as described in connection with FIG. 1. The sample was fixed onto an aluminum mount and carbon is vapour-deposited onto it under vacuum. The micrograph was taken at a working distance of 13 mm and an acceleration voltage of 5 kV using a Zeiss DSM 982 Gemini raster electron microscope (Zeiss, Oberkochen, Germany). FIG. 4 shows that, through the electrostatic flocking, nearly all fibers 3 are arranged in an ordered, almost perpendicular orientation to the surface of the base material 1. The fibers 3 project into the adhesive layer 2 with their lower ends and are thereby firmly connected with the base material 1. As a result of capillary forces on the fibers 3 and the drying action, the adhesive layer 2 is thicker in immediate vicinity to the fibers 3. The adhesive layer 2 forms thereby a kind of socket round the lower ends of the fibers 3. The fibers 3 at the front edge are somewhat bent to the side as a consequence of cutting out the sample with scissors.

Figure 5:
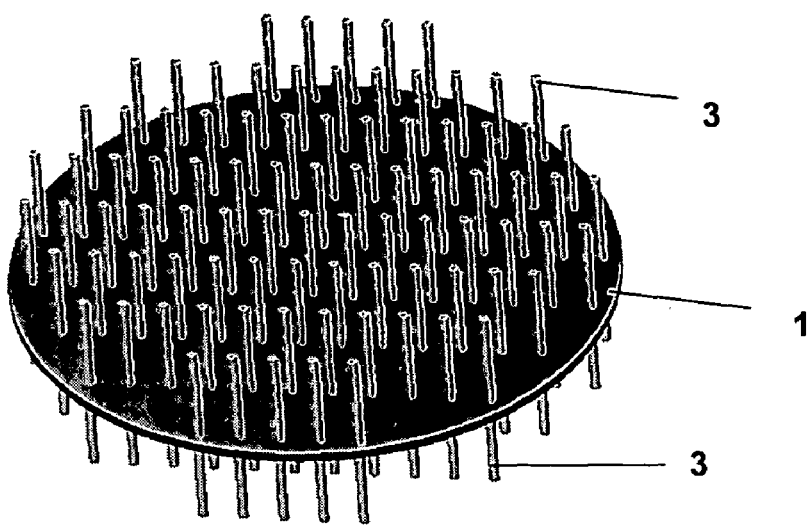
FIG. 5. a three-dimensional illustration of a scaffold with base material flocked on both sides.

The scaffold of FIG. 5 flocked with fibers on both sides is constructed from the same materials as those described in connection with FIG. 1. It contains also an adhesive layer between the fibers 3 and the base material 1, which is not shown for reasons of clarity. For producing this scaffold having a base material 1 flocked on both sides, a collagen tape 1, as described in connection with FIG. 1, is first flocked electrostatically on one side with fibers 3. The scaffold thus formed is then turned round and flocked with fibers 3 in the same way as described in connection with FIG. 1. The tape 1 flocked on both sides is subsequently freeze-dried and crosslinked as described in connection with FIG. 1.

Figure 6:
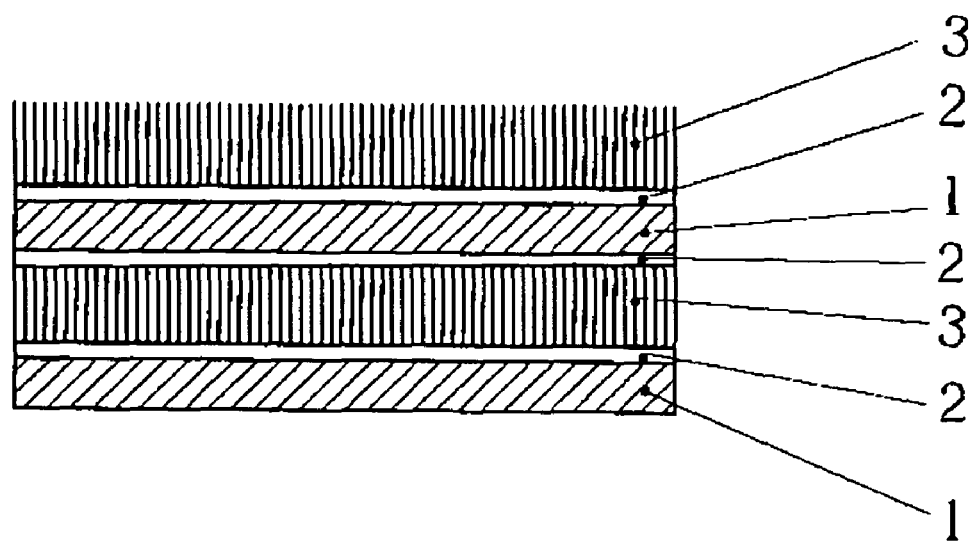
FIG. 6. a sectional view of a two-layered scaffold.

FIG. 6 shows a two-layered scaffold. It is comprised of two scaffolds, in which the base materials 1 are flocked with fibers 3 on one side and which are constructed analogously to those described in connection with FIG. 1. In addition, the two-layered scaffold contains an adhesive layer 2 between both scaffolds. The fiber material 3 here consists of polylactide (PLA), a biocompatible and resorbable material with a Young's Modulus of 5 to 7 GPa. The fibers 3 have a length of 1 mm and a diameter of 30 μm.

The procedure for the production of the two-layered scaffold material is as follows: two scaffolds were produced, analogue to those described in connection with FIG. 1. However the aforementioned fibers 3 made out of PLA are used as fibers 3. On the non-flocked side of the first scaffold, a gelatine solution, produced as described in connection with FIG. 1, with an adhesive thickness 2 of 0.02 mm is applied. The side of the first scaffold coated with adhesive 2 is now placed onto the flocked side of the second scaffold. The two-layered scaffold thus produced is freeze-dried and crosslinked, as described in FIG. 1.

Figure 7:
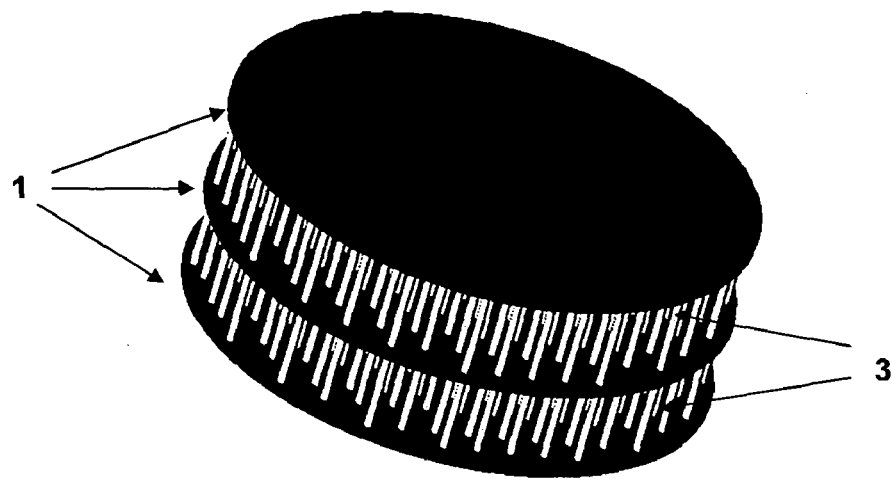
FIG. 7. a three-dimensional representation of a three-layered scaffold.

The three-layered scaffold of FIG. 7 is put together from two scaffolds with base materials 1 flocked on one side and one scaffold with a base material flocked on both sides. The scaffolds with base materials 1 flocked on one side are constructed and produced as described in connection with FIG. 1. The scaffolds with base materials 1 flocked on both sides are constructed and produced as described in connection with FIG. 6. For the production of this multilayered scaffold, the fiber layer of the individual scaffolds with base materials 1 flocked on one side is inserted, respectively, into a fiber layer of the scaffold with a base material 1 flocked on both sides. By inserting the fiber layers into each other, the scaffolds hold together analogous to a hook-and-loop fastener principle, without requiring an additional adhesive layer.

Figure 8:
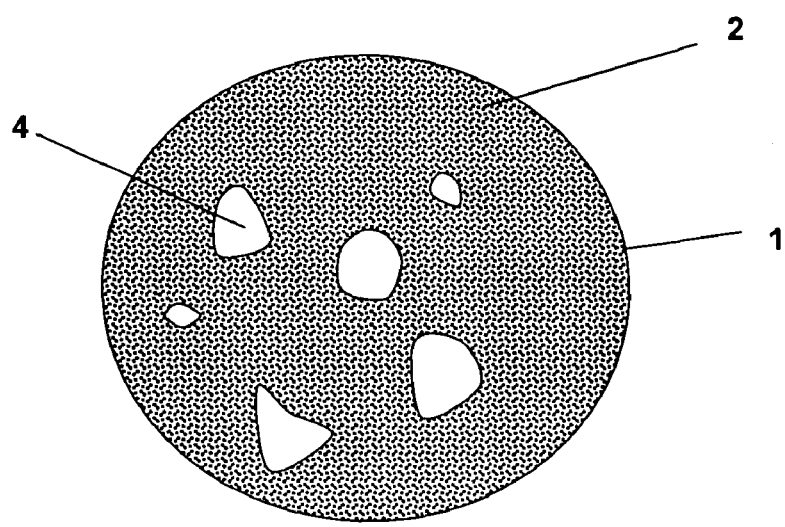
FIG. 8. a plan view of a partially unflocked scaffold.

The partially unflocked scaffold shown in FIG. 8 is not flocked with fibers in systematically selected regions 4. In regard to the materials, the scaffold is constructed as described in connection with FIG. 1 and flocked as described in connection with FIG. 1. The non-flocked areas 4 are formed by the application of an adhesive 2, as described in connection with FIG. 1, corresponding to the pattern of a silk-screen template by means of a silk-screen template commonly used in flocking. The base materials 1 partially coated by adhesive 2 according to the pattern are flocked as described in FIG. 1, whereby no fibers 3 are bonded where adhesive-free surfaces are present.

Figure 9:
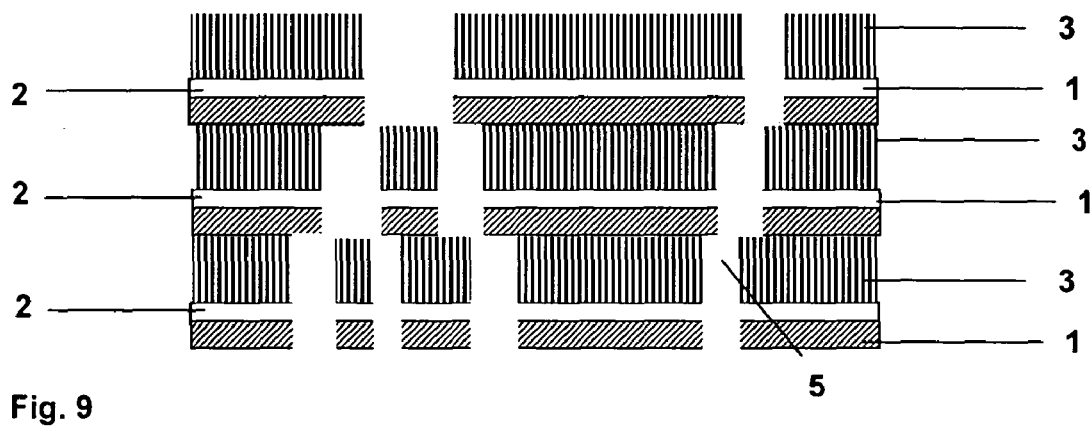
FIG. 9. a sectional plane through a multilayered scaffold with vessel-like cavities.

FIG. 9 shows a three-layered scaffold with cavities 5. It is constructed from three scaffolds with base materials 1 flocked on one side. These scaffolds contain defined, but different holes (perforations). A cutting step performed subsequently has the advantage that the flocking fibers at the edge of the hole are arranged almost perpendicularly.

To produce this multilayered scaffold with cavities 5, holes are punched post-flocking in three scaffolds constructed and produced as described in connection with FIG. 1. The thus perforated scaffolds are stacked on top of one another, wherein the holes are partially arranged on top of one another. Through this arrangement, pipe-shaped cavities are formed in the three-dimensional multilayered scaffold. During a later colonization with cells, these cavities serve for supplying nutrients and oxygen to the cells, among other things.

Figure 10:
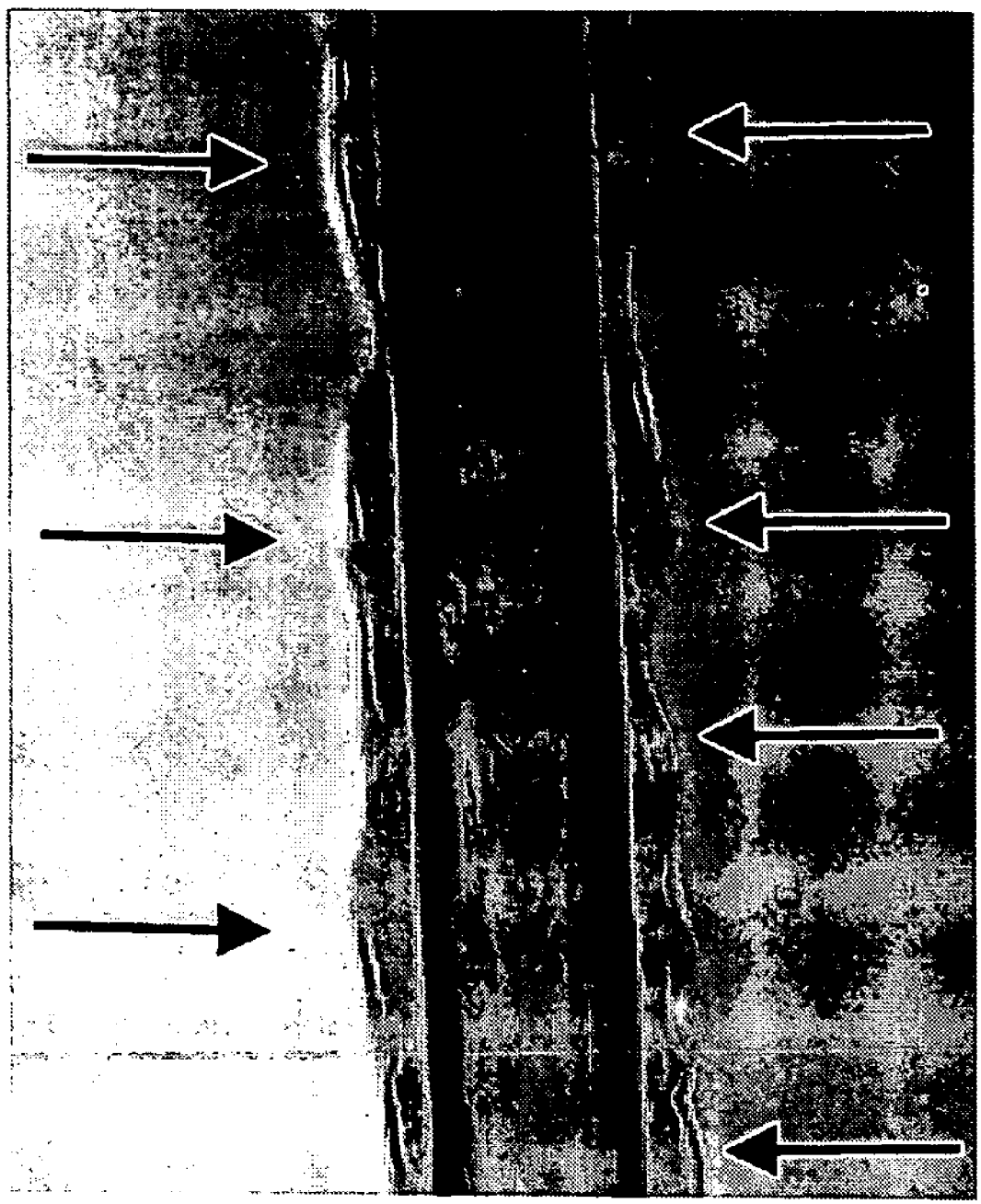
FIG. 10. a light-microscope micrograph of a PHB-fiber, seeded with fibroblasts, in a scaffold.

The light microscope micrograph of FIG. 10 shows a PHB-fiber colonized by fibroblasts in a scaffold. The arrangement of individual cells is indicated by arrows.

The structure and production of an implant with the scaffold according to the invention will be explained more precisely in the following using a cartilage replacement material as an example.

The scaffold here consists of a base material layer of a mineralized hydroxyapatite-collagen tape with a diameter of 7 cm and a mean thickness of 0.3 mm. Biocompatible and resorbable short fibers of polyhydroxybutyrate with a fiber length of 1 mm are used as fiber material for the electrostatic flocking. The Pharma-Gelatine of DGF Stoess AG is used as adhesive. The scaffold material was flocked on one side as described in connection with FIG. 1, freeze-dried, and a sample with a diameter of 13 mm was punched out. The scaffold thus produced is characterized by a flocking fiber density of 260 fibers/mm$^2$, a compressive strength of $\sigma_D$=0.11 MPa (linear elastic behavior), a compressive modulus of E=0.21 MPa, a fiber pull-out strength of $\sigma_F$=0.46 Mpa, and fiber spacings between 50 μm and 100 μm.

A structurally elastic knitted-fabric hose of polyhydroxybutyrate is pulled as an envelope over the punched-out sample. The knitted-fabric hose is produced from polyhydroxybutyrate fibers on a straight-bar knitting machine CMS 211 of the company Stoll with a gauge of E18. The enveloped scaffold is sterilized by irradiation with gamma radiation.

For colonization with cartilage cells, the enveloped scaffold is first placed in 5 ml sterile cell culture medium (DMEM, Sigma GmbH, Munich, Germany) for 24 hours. The medium is changed every 6 hours. Subsequently, the sample is taken out of the medium and dried to some extent on a sterile, absorbent towel. The sample is now transferred to a customary 24-well cell culture plate with the flocked side up and a suspension of $1\times10^5$ primary human chondrocytes in 1 ml cell culture medium is applied with a pipette. The cell culture plate is now incubated for 24 hours in a typical cell culture incubator under standard conditions. During this time the adhesion of the chondrocytes to the scaffold takes place. Subsequently, the thus seeded scaffold is transferred to fresh medium and cultivated, including changing of the medium three times weekly, under standard conditions until further use.

During the incubation, the chondrocytes settle predominantly on and between the fibers. By applying ultrasound or pressure on the surface of the enveloped scaffold, a mechanical loading is simulated in vitro, which approximates the natural loading of the chondrocytes in joint cartilage in vivo. Here, the flocking fibers simulate the natural matrix of the cartilage and take up a part of the load.

When implanted in the human body, the enveloped scaffold is placed on areas of a joint, where the cartilage is degenerated or damaged. The side of the scaffold flocked with fibers is arranged in the direction of the joint surface. The unflocked side lies on the degenerated cartilage or bone respectively, or is turned towards the bone side.

For areas of the surface of a joint, which carry heavy loads, a polyhydroxybutyrate-based tape is used as the base material of the scaffold for the scaffold production in place of the collagen tape. The flocking process and the colonization with chondrocytes is carried out correspondingly.

When implanted, the cell-colonized scaffold is arranged with the unflocked, relatively smooth surface towards the surface of the joint. Through this arrangement, the friction between joint and implant is reduced.

What is claimed is:

1. A biocompatible scaffold for tissue culture and cell culture and for producing implants or implant materials, the scaffold comprised of at least one base material in the form of a three-dimensional body and fibers connected to at least one side of the three-dimensional body, wherein the fibers are connected to the at least one side by electrostatic flocking and by electrostatic flocking are arranged on the at least one side substantially perpendicular to a surface of said at least one side, wherein the at least one base material and the fibers are comprised of a resorbable material, respectively, wherein the resorbable material of the fibers is a resorbable polymer, and wherein the resorbable material of the at least one base material is selected from the group consisting of collagen, collagen derivatives, hyaluronic acid, chitosan, gelatine, and composites thereof.

2. The scaffold according to claim 1, wherein the resorbable material of the fibers is selected from the group consisting of polylactide; polycaproplactone; polyhydroxybutyrate; polyglycolide; derivatives of polylactide, polycaproplactone, polyhydroxybutyrate, or polyglycolide; and copolymers of polylactide, polycaproplactone, polyhydroxybutyrate, or polyglycolide.

3. A biocompatible scaffold for tissue culture and cell culture and for producing implants or implant materials, the scaffold comprised of at least one base material in the form of a three-dimensional body, an adhesive covering at least one side of the three-dimensional body, and fibers connected by the adhesive to the at least one side and applied by electrostatic flocking.

4. The scaffold according to claim 3, wherein at least one of the at least one base material, the adhesive, and the fibers are comprised of a resorbable material.

5. The scaffold according to claim 4, wherein the resorbable material of the fibers is a resorbable polymer; wherein the resorbable material of the base material is selected from the group consisting of collagen; collagen derivatives; hyaluronic acid; chitosan; gelatine; and composites thereof.

6. The scaffold according to claim 5, wherein the resorbable material of the adhesive is selected from the group consisting of collagen; collagen derivatives; hyaluronic acid; chitosan; gelatine; and composites thereof.

7. The scaffold according to claim 5, wherein the resorbable material of the fibers is selected from the group consisting of polylactide; polycaproplactone; polyhydroxybutyrate; polyglycolide; derivatives of polylactide, polycaproplactone, polyhydroxybutyrate, or polyglycolide; and copolymers of polylactide, polycaproplactone, polyhydroxybutyrate, or polyglycolide.

8. A biocompatible scaffold for tissue culture and cell culture and for producing implants or implant materials, the scaffold comprised of at least one base material and fibers that are electrostatically flocked onto at least one side of the at least one base material, wherein the fibers have a length between 0.3 mm and 3 mm.

9. The scaffold according to claim 8, wherein the fibers have a diameter of between 10 μm and 200 μm.

10. A biocompatible scaffold for tissue culture and cell culture and for producing implants or implant materials, the scaffold comprised of at least one base material and fibers that are electrostatically flocked onto at least one side of the at least one base material, wherein the fibers are arranged on the base material so as to have a mean distance from 40 μm to 250 μm.

11. The scaffold according to claim 10, wherein the fibers have a diameter of between 10 μm and 200 μm.

12. A biocompatible scaffold for tissue culture and cell culture and for producing implants or implant materials, the scaffold comprised of at least one base material and fibers that are electrostatically flocked onto at least one side of the at least one base material, wherein at least some of the fibers are hollow fibers.

13. The scaffold according to claim 3, further comprising cells colonized on the scaffold.

14. A multi-layered scaffold structure comprising at least two biocompatible scaffolds according to claim 3 that are connected to one another.

15. The multi-layered scaffold structure according to claim 14, wherein the at least two biocompatible scaffolds are stacked on top of one another.

16. The multi-layered scaffold structure according to claim 15, wherein the at least two biocompatible scaffolds are inserted into one another with the at least one side flocked with the fibers.

17. The multi-layered scaffold structure according claim 14, comprising cavities or a system of cavities.

18. An implant material comprising a biocompatible scaffold according to claim 3 or a multi-layered scaffold structure according to claim 14.

19. The implant material according to claim 18, further comprising an envelope surrounding the biocompatible scaffold or the multi-layered scaffold structure.

20. The implant material according to claim 19, wherein the envelope is a textile fabric, a film, or a tape.

21. An implant comprising a biocompatible scaffold according to claim 20 or a multi-layered scaffold structure according to claim 14.

22. The implant according to claim 21, further comprising an envelope surrounding the biocompatible scaffold or the multi-layered scaffold structure.

23. The implant according to claim 22, wherein the envelope is a textile fabric, a film, or a tape.

24. The scaffold according to claim 1, wherein the composites are collagen-hyaluronic acid composites or hydroxyapatite collagen composites.

25. The scaffold according to claim 5, wherein the composites are collagen-hyaluronic acid composites or hydroxyapatite collagen composites.

26. A process for producing a tissue culture or a cell culture or an implant material, comprising the steps of:
 a) introducing cells into a biocompatible scaffold according to claim 3;
 b) incubating the cells in the scaffold for colonizing the scaffold with cells and forming an extra-cellular matrix.

27. An implant material containing cells and an extra-cellular matrix, produced by the steps of:
 a) introducing cells into a biocompatible scaffold according to claim 3;
 b) incubating the cells in the scaffold for colonizing the scaffold with cells and forming an extra-cellular matrix;
 c) removing the base material of the biocompatible scaffold after the extra-cellular matrix has been formed.

* * * * *